(12) United States Patent
Heilek et al.

(10) Patent No.: US 7,705,181 B2
(45) Date of Patent: Apr. 27, 2010

(54) PROCESS FOR REMOVING METHACRYLIC ACID FROM LIQUID PHASE COMPRISING ACRYLIC ACID AS A MAIN CONSTITUENT AND TARGET PRODUCT, AND METHACRYLIC ACID AS A SECONDARY COMPONENT

(75) Inventors: Jörg Heilek, Bammental (DE); Klaus Joachim Müller-Engel, Stutensee (DE); Christoph Adami, Weinheim (DE); Martin Dieterle, Mannheim (DE)

(73) Assignee: BASF Akiengesellschaft, Ludwigshafen (DE)

( * ) Notice: Subject to any disclaimer, the term of this patent is extended or adjusted under 35 U.S.C. 154(b) by 0 days.

(21) Appl. No.: 11/354,101

(22) Filed: Feb. 15, 2006

(65) Prior Publication Data

US 2006/0199976 A1 Sep. 7, 2006

Related U.S. Application Data

(60) Provisional application No. 60/668,089, filed on Apr. 5, 2005, provisional application No. 60/656,877, filed on Mar. 1, 2005.

(30) Foreign Application Priority Data

Mar. 1, 2005 (DE) ............... 10 2005 009 890
Apr. 5, 2005 (DE) ............... 10 2005 015 639

(51) Int. Cl.
*C07C 51/42* (2006.01)
(52) U.S. Cl. .................................... 562/600
(58) Field of Classification Search .......... 562/598, 562/600
See application file for complete search history.

(56) References Cited

U.S. PATENT DOCUMENTS

| | | | |
|---|---|---|---|
| 3,161,670 A | 12/1964 | Adams et al. | |
| 4,317,926 A | 3/1982 | Sato et al. | |
| 4,413,147 A | 11/1983 | Khoobiar | |
| 5,087,744 A | 2/1992 | Krabetz et al. | |
| 5,198,578 A | 3/1993 | Etzkorn et al. | |
| 5,426,221 A | 6/1995 | Willersinn | |
| 5,504,247 A * | 4/1996 | Saxer et al. ............... | 562/600 |
| 5,780,679 A | 7/1998 | Egly et al. | |
| 5,793,391 A | 8/1998 | Kawakami et al. | |
| 5,821,390 A | 10/1998 | Ruppel et al. | |
| 5,831,124 A | 11/1998 | Machhammer et al. | |
| 5,897,749 A | 4/1999 | Kroker et al. | |
| 6,063,959 A | 5/2000 | Lehnert et al. | |
| 6,207,022 B1 | 3/2001 | Dockner et al. | |
| 6,350,906 B2 | 2/2002 | Machhammer et al. | |
| 6,413,379 B1 | 7/2002 | Machhammer et al. | |
| 6,448,439 B1 * | 9/2002 | Eck et al. ................. | 562/600 |
| 6,498,272 B1 | 12/2002 | Schröder et al. | |
| 6,555,707 B1 | 4/2003 | Nestler et al. | |
| 6,596,901 B1 | 7/2003 | Eck et al. | |
| 6,646,161 B1 | 11/2003 | Eck et al. | |
| 6,679,939 B1 | 1/2004 | Thiel et al. | |
| 6,700,016 B1 | 3/2004 | Eck et al. | |
| 6,727,383 B1 | 4/2004 | Nestler et al. | |
| 6,781,017 B2 | 8/2004 | Machhammer et al. | |
| 6,852,881 B2 | 2/2005 | De Decker et al. | |
| 6,921,837 B2 | 7/2005 | Eck et al. | |
| 6,939,991 B2 | 9/2005 | Thiel et al. | |
| 2001/0007043 A1 | 7/2001 | Machhammer et al. | |
| 2003/0040570 A1 * | 2/2003 | Nestler et al. ............... | 524/558 |
| 2003/0060661 A1 | 3/2003 | Eck et al. | |
| 2003/0149301 A1 | 8/2003 | Eck et al. | |
| 2003/0175159 A1 | 9/2003 | Heilek et al. | |
| 2003/0187299 A1 | 10/2003 | Machhammer et al. | |
| 2004/0063988 A1 | 4/2004 | Hechler et al. | |
| 2004/0063989 A1 | 4/2004 | Hechler et al. | |
| 2004/0097756 A1 | 5/2004 | Thiel et al. | |
| 2004/0116736 A1 | 6/2004 | Machhammer et al. | |
| 2004/0133015 A1 | 7/2004 | Hammon et al. | |
| 2004/0138501 A1 | 7/2004 | Thiel et al. | |
| 2004/0147763 A1 | 7/2004 | Hammon et al. | |
| 2004/0171887 A1 | 9/2004 | Berndt et al. | |
| 2004/0181083 A1 | 9/2004 | Proll et al. | |
| 2004/0242826 A1 | 12/2004 | Nishimura | |
| 2004/0256319 A1 | 12/2004 | Hammon et al. | |
| 2005/0005399 A1 | 1/2005 | Lu et al. | |
| 2005/0090628 A1 | 4/2005 | Eck et al. | |
| 2005/0119515 A1 | 6/2005 | Machhammer et al. | |

FOREIGN PATENT DOCUMENTS

DE 33 13 573 A1 10/1983

(Continued)

OTHER PUBLICATIONS

"Methacrylic Acid and Derivatives" in Kirk-Othmer Encyclopedia of Chemical Technology, Copyright © 2001 by John Wiley & Sons, Inc., pp. 227-270.*

*Primary Examiner*—Karl J Puttlitz
(74) *Attorney, Agent, or Firm*—Oblon, Spivak, McClelland, Maier & Neustadt, L.L.P.

(57) ABSTRACT

A process for removing methacrylic acid from liquid phase P comprising acrylic acid as a main constituent and target product, and methacrylic acid as a secondary component in which the removal is effected by crystallization, the acrylic acid accumulating in the crystals formed and the methacrylic acid in the remaining mother liquor.

24 Claims, No Drawings

FOREIGN PATENT DOCUMENTS

| | | |
|---|---|---|
| DE | 35 21 458 A1 | 12/1985 |
| DE | 43 08 087 A1 | 9/1994 |
| DE | 43 35 172 A1 | 4/1995 |
| DE | 44 36 243 A1 | 4/1996 |
| DE | 196 06 877 A1 | 8/1997 |
| DE | 196 27 847 A1 | 1/1998 |
| DE | 197 40 252 A1 | 3/1999 |
| DE | 197 40 253 A1 | 3/1999 |
| DE | 198 38 845 A1 | 3/2000 |
| DE | 199 24 532 A1 | 11/2000 |
| DE | 199 24 533 A1 | 11/2000 |
| DE | 101 15 277 A1 | 6/2002 |
| DE | 101 22 787 A1 | 6/2002 |
| DE | 101 31 297 A1 | 1/2003 |
| DE | 102 35 847 A1 | 8/2003 |
| DE | 102 19 686 A1 | 11/2003 |
| DE | 102 23 058 A1 | 12/2003 |
| DE | 103 36 386 A1 | 3/2004 |
| DE | 102 43 625 A1 | 4/2004 |
| DE | 102 45 585 A1 | 4/2004 |
| DE | 102 46 119 A1 | 4/2004 |
| DE | 103 32 758 A1 | 5/2004 |
| EP | 0 117 146 A1 | 8/1984 |
| EP | 0 297 445 A2 | 1/1989 |
| EP | 0 608 838 A2 | 8/1994 |
| EP | 0 616 998 A1 | 9/1994 |
| EP | 0 648 732 A1 | 4/1995 |
| EP | 0 695 736 A1 | 2/1996 |
| EP | 0 700 714 A1 | 3/1996 |
| EP | 0 700 893 A1 | 3/1996 |
| EP | 0 792 867 A2 | 9/1997 |
| EP | 0 854 129 A1 | 7/1998 |
| EP | 0921113 * | 12/1998 |
| EP | 0 920 408 | 6/1999 |
| EP | 0 982 287 A1 | 3/2000 |
| EP | 0 982 288 A2 | 3/2000 |
| EP | 0 982 289 A2 | 3/2000 |
| EP | 0 990 636 A1 | 4/2000 |
| EP | 1 015 410 | 7/2000 |
| EP | 1 015 411 | 7/2000 |
| EP | 1 041 062 A2 | 10/2000 |
| EP | 1 066 239 | 1/2001 |
| EP | 1 066 240 | 1/2001 |
| EP | 1 068 174 | 1/2001 |
| EP | 1 159 249 | 12/2001 |
| EP | 1 163 201 | 12/2001 |
| EP | 1 189 861 | 3/2002 |
| EP | 1 305 097 | 5/2003 |
| EP | 1 252 129 B1 | 1/2004 |
| EP | 1 388 532 A1 | 2/2004 |
| EP | 1 388 533 A1 | 2/2004 |
| EP | 1 484 303 A2 | 12/2004 |
| EP | 1 484 308 A1 | 12/2004 |
| EP | 1 484 309 A1 | 12/2004 |
| GB | 2 160 543 A | 12/1985 |
| WO | WO 98/01414 | 1/1998 |
| WO | WO 98/01415 | 1/1998 |
| WO | WO 99/14181 | 3/1999 |
| WO | WO 99/14182 | 3/1999 |
| WO | WO 99/50219 | 10/1999 |
| WO | WO 99/50220 | 10/1999 |
| WO | WO 99/50222 | 10/1999 |
| WO | WO 00/53560 | 9/2000 |
| WO | WO 00/53561 | 9/2000 |
| WO | WO 00/75097 A1 | 12/2000 |
| WO | WO 01/77056 A1 | 10/2001 |
| WO | WO 01/92197 A1 | 12/2001 |
| WO | WO 01/96270 A2 | 12/2001 |
| WO | WO 01/96271 A2 | 12/2001 |
| WO | WO 02/09839 A1 | 2/2002 |
| WO | WO 02/055469 A1 | 7/2002 |
| WO | WO 02/055496 A1 | 7/2002 |
| WO | WO 02/090310 A1 | 11/2002 |
| WO | WO 03/011804 A2 | 2/2003 |
| WO | WO 03/041832 A1 | 5/2003 |
| WO | WO 03/041833 A1 | 5/2003 |
| WO | WO 03/076370 A1 | 9/2003 |
| WO | WO 03/078378 A1 | 9/2003 |
| WO | WO 2004/035514 A1 | 4/2004 |
| WO | WO 2004/063138 A1 | 7/2004 |

* cited by examiner

PROCESS FOR REMOVING METHACRYLIC ACID FROM LIQUID PHASE COMPRISING ACRYLIC ACID AS A MAIN CONSTITUENT AND TARGET PRODUCT, AND METHACRYLIC ACID AS A SECONDARY COMPONENT

BACKGROUND OF THE INVENTION

1. Field of the Invention

The present invention relates to a process for removing methacrylic acid from liquid phase comprising acrylic acid as a main constituent and target product, and methacrylic acid as a secondary component.

2. Description of the Background

Acrylic acid is an important monomer which finds use as such or in the form of its alkyl esters for obtaining, for example, polymers suitable as adhesives or water-superabsorbent polymers (cf., for example, WO 02/055469 and WO 03/078378).

Acrylic acid is prepared on the industrial scale worldwide virtually exclusively by the (generally two-stage) heterogeneously catalyzed partial oxidation process of propylene (cf., for example, EP-A 990 636, U.S. Pat. No. 5,198,578, EP-A 10 15 410, EP-A 14 84 303, EP-A 14 84 308, EP-A 14 84 309 and US-A 2004/0242826). The starting propylene used is propylene of comparatively high purity (cf. DE-A 101 31 297). It is relatively inconvenient and costly to obtain such pure crude propylene. It normally originates from crude paraffinic hydrocarbons and generally includes various purification stages in order to isolate the propylene formed in highly pure form (cf. DE-A 35 21 458). These purification stages generally comprise separations from olefins other than propylene and from other secondary products other than propylene, including the secondary components already comprised in the crude paraffinic hydrocarbon.

Of particular significance in this context is the separation of propylene from its companion propane. Owing to the physical similarity of the two compounds, this removal in particular is capital- and energy-intensive. Since the predominant amount of the thus obtained crude propylene is used in large amounts for subsequent polymerizations (for example to prepare polypropylene), (where the high purity described is indispensable) and experiences a high addition of value, the aforementioned removals are customary in conjunction with refinery crackers and steamcrackers in spite of the associated cost and inconvenience, and form the state of the art in industry. The proportion of these crude propylenes flowing into the partial oxidation to acrylic acid is of rather minor importance compared to the demand for polypropylene, and is a secondary demand stream at raw material prices which are still acceptable.

It is characteristic of the preparation of acrylic acid by catalytic partial oxidation in the gas phase of such comparatively pure propylene that the acrylic acid, in spite of the available purity of the raw material, is not obtained as such, but rather, especially owing to parallel side reactions, as a constituent of a product gas mixture from which it subsequently has to be removed.

This product gas mixture generally also comprises reactants which have not been converted fully, if appropriate intermediates which have not been converted fully and, for reasons of improved heat transfer and to ensure nonexplosive behavior, additionally used inert diluent gas.

In this document, an inert diluent gas shall be understood to be a reaction gas constituent which behaves inertly under the conditions of the relevant reaction and, each inert reaction gas constituent viewed alone, remains chemically unchanged to an extent of more than 95 mol %, preferably to an extent of more than 97 mol %, or 98 mol % or 99 mol %.

A common feature of substantially all separation processes known in this regard is that, if appropriate after direct and/or indirect cooling of the aforementioned product gas mixture, acrylic acid comprised in the product gas mixture is transferred in a basic removal step into the condensed (especially liquid) phase.

This may be effected, for example, by absorption into a suitable solvent (e.g. water, high-boiling organic solvents, aqueous solutions) and/or by partial or substantially full condensation (e.g. fractional condensation) (on this subject, see the documents cited at the outset, and also the documents EP-A 13 88 533, EP-A 13 88 532, DE-A 102 35 847, EP-A 79 28 67, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 85 41 29, U.S. Pat. No. 4,317,926, DE-A 198 37 520, DE-A 196 06 877, DE-A 190 50 1325, DE-A 102 47 240, DE-A 197 40 253, EP-A 69 57 36, EP-A 98 22 87, EP-A 10 41 062, EP-A 11 71 46, DE-A 43 08 087, DE-A 43 35 172, DE-A 44 36 243, DE-A 19 924 532, DE-A 103 32 758 and DE-A 19 924 533). A removal of acrylic acid may also be undertaken as described in EP-A 98 22 87, EP-A 98 22 89, DE-A 103 36 386, DE-A 101 15 277, DE-A 196 06 877, DE-A 197 40 252, DE-A 196 27 847, EP-A 92 04 08, EP-A 10 68 174, EP-A 10 66 239, EP-A 10 66 240, WO 00/53560, WO 00/53561, DE-A 100 53 086 and EP-A 98 22 88. Favorable ways of removal are also the processes described in the documents WO 2004/063138, WO 2004/035514, DE-A 102 43 625 and DE-A 102 35 847.

The further removal of the acrylic acid from the liquid (condensed) phases which comprise the acrylic acid target product and are obtained in the basic separation described is undertaken in the processes of the known prior art, depending on the other by-products, in particular those dependent upon the specific catalysts used for the partial oxidation and other selected partial oxidation conditions, comprised in addition to acrylic acid, by a wide variety of combinations of extractive, desorptive, rectificative, azeotropically distillative and/or crystallizative processes up to the desired degree of purity of the acrylic acid. Particularly high purity demands are made on the acrylic acid when it is to be used to prepare water-superabsorbent polymers (polyacrylic acids or alkali metal salts thereof), since such polymers find use in particular in the hygiene sector, where medical standards apply. The aim of the predominant number of acrylic acid preparation processes is therefore a very economically viable route to such glacial acrylic acid suitable for superabsorbents.

A characteristic feature of the conventional acrylic acid preparation route described is that it includes by-product formation of methacrylic acid at most in amounts which are analytically undetectable or analytically insignificant, which can be attributed primarily to the high degree of purity of the crude propylene used. Thus, none of the following prior art documents even mentions methacrylic acid as a possible secondary component of acrylic acid, even though the majority of these documents comprise highly detailed secondary component analyses: WO 98/01414, WO 01/92197, EP-A 648 732, EP-A 1305097, EP-A 14 84 308, EP-A 14 84 309, US-A 2004/0242826, DE-A 103 36 386, WO 02/055469, WO 03/078378, WO 01/77056, WO 03/041833, DE-A 196 06 877, EP-A 792 867, EP-A 920 408, EP-A 10 15 411, EP-A 10 15 410, DE-A 198 38 845, WO 03/041833, WO 02/090310, DE-A 101 22 787, WO 03/041832, EP-A 10 68 174, EP-A 10 66 239, EP-A 11 63 201, EP-A 11 59 249, EP-A 11 89 861, EP-A 1 252 129, WO 01/77056, DE-A 102 35 847, DE-A 102 43 625 and WO 2004/035514. The same statement applies to the documents referred to as the particular state of the art in the aforementioned documents.

On the other hand, methacrylic acid, as would then be formed as a secondary component companion in a preparation of acrylic acid, would be a particularly unpleasant companion to acrylic acid which would not remain unmentioned in the prior art. This would be the case in particular because the tendency of methacrylic acid to free-radical polymerization, owing to the positive inductive effect of the methyl group which distinguishes it from acrylic acid, is significantly reduced in comparison to the same tendency of acrylic acid.

In other words, when acrylic acid which comprises methacrylic acid even only in traces is used to prepare watersuperabsorbent free-radically polymerized polymers, it has to be assumed that the methacrylic acid is not sufficiently polymerized under the particular polymerization conditions selected and remains in the polymer formed as a vinylically unsaturated compound, which is problematic in applications in the hygiene sector. Presence of methacrylic acid can also adversely effect the polymer quality (for example molecular weight distribution, degree of crosslinking, etc.).

In the search for a more economically viable propylene source which can be used for a heterogeneously catalyzed partial oxidation to acrylic acid, it has also already been proposed to start from crude propane and convert it, in a reaction stage preceding the propylene partial oxidation, by homogeneous and/or heterogeneously catalyzed oxydehydrogenation and/or heterogeneously catalyzed dehydrogenation, partially to propylene, and to use the latter for the relevant partial oxidation without removing it in a costly and inconvenient manner from unconverted propane (cf., for example, WO 03/076370, WO 01/96271, EP-A 117 146, WO 03/011804, U.S. Pat. No. 3,161,670, DE-A 33 13 573, WO 01/96270 and the prior art referred to in these documents). According to DE-A 102 46 119 and DE-A 102 45 585, the procedure should be such that suitable separation steps ensure that the resulting starting reaction gas mixture for the propylene partial oxidation comprises a minimum level of $C_4$ hydrocarbons as undesired impurities which impair the catalyst performance. A disadvantage of such a procedure is that the aforementioned separation operations are costly and inconvenient, and are economically in some cases prohibitive for crude propylene envisaged merely as an acrylic acid raw material, or achieve only limited separating action when they are employed more economically.

At the same time, crude propanes which comprise saturated or unsaturated $C_4$ hydrocarbons to a significant extent are available particularly inexpensively on the market, whether they occur as poorly utilizable secondary streams on the route to the preparation of ultrapure crude propane or a costly and inconvenient $C_3/C_4$ hydrocarbon separation has been dispensed with fully in the course of their generation.

In the individual case such a favorable raw material price is then capable of economically overcompensating an accompanying reduction in the catalyst performance in a downstream heterogeneously catalyzed acrylic acid preparation by partial oxidation, or a premature requirement for a catalyst change.

A remaining disadvantage of a procedure for preparing acrylic acid which might otherwise be attractive as described is that it is accompanied, depending on catalysts used for the heterogeneously catalyzed partial oxidation of propylene afflicted with corresponding $C_4$ hydrocarbon contents to prepare acrylic acid, by methacrylic acid secondary component formation owing to a partial oxidation of the $C_4$ hydrocarbons (e.g. isobutene and isobutane) proceeding in parallel to the main propylene partial oxidation, with the disadvantages described (cf. DE-A 102 19 686, DE-A 33 13 573 and EP-A 297 445). The same disadvantages may accrue depending on the catalyst and reaction conditions used when acrylic acid is obtained by partial direct oxidation of propane comprising $C_4$ hydrocarbons as impurities, as is detailed, for example, in EP-A 608 838, DE-A 198 35 247, and also the documents DE-A 102 45 585 and DE-A 102 46 119. Another possible $C_3$ precursor which may be burdened with $C_4$ hydrocarbons or their oxidative derivatives for a heterogeneously catalyzed preparation by partial oxidation of acrylic acid is acrolein (cf. EP-A 700 893 and EP-A 700 714).

SUMMARY OF THE INVENTION

It was therefore an object of the present invention to provide a very efficient process for removing methacrylic acid from liquid phase comprising acrylic acid as a main constituent and target product, and methacrylic acid as a secondary component.

Accordingly, a process has been found for removing methacrylic acid from liquid phase P comprising acrylic acid as a main constituent and target product, and methacrylic acid as a secondary component, which comprises effecting the removal by crystallization, the acrylic acid accumulating in the crystals formed and the methacrylic acid in the remaining mother liquor.

DETAILED DESCRIPTION OF THE PREFERRED EMBODIMENTS

A procedure as described above is efficient only when there is substantially no incorporation of methacrylic acid into the crystal in the course of the formation of an acrylic acid crystal. This is generally the case when the depletion coefficient $A^{MAS}$ associated with the crystallization is $\geqq 15$. The depletion coefficient A is understood generally to be the ratio of impurity remaining in the mother liquor to impurity remaining in the crystals (in each case expressed as % by weight based on the total amount of mother liquor or the total amount of crystals; for example, mother liquor and crystals can be separated substantially fully from one another by centrifugation or by centrifugation and/or washing, and can be determined by subsequent analysis A; to this end, a mother liquor removal to an extent of more than 90% by weight, preferably to an extent of more than 95% by weight, or 97 or 98% by weight, or 99% by weight, of its total amount is generally sufficient).

In the case of acetic acid ($A^{ES}$) and propionic acid ($A^{PS}$) as acrylic acid impurities, the depletion coefficient is typically at values of $\leqq 10$. In other words, they are also incorporated into the acrylic acid crystals and can only be extracted from these crystals with difficulty, for example by suitable washing. In other words, a crystallizative removal of these two impurities from acrylic acid generally entails the use of low-efficiency and capital-intensive multistage crystallization processes, as are recommended, for example, in EP-A 616 998 in the form of a multistage combination of dynamic and static crystallization and which, in addition to the multistage process, require at least one dynamic and at least one static crystallizer. At best under particular boundary conditions of crystallization (cf. in particular WO 03/078378 and WO 01/77056), acrylic acid crystal forms are formed, from which acetic acid and propionic acid can be removed comparatively readily by subsequent washing with pure acrylic acid melt.

The greater $A^{MAS}$ is, the more attractive a crystallizative removal of methacrylic acid from acrylic acid is.

As a result of detailed investigations, it has been found that, surprisingly, in the crystallizative removal of methacrylic acid from liquid phase comprising acrylic acid as a main constituent and target product, and methacrylic acid as a secondary component, even unaccompanied centrifugal mother liquor/crystals removal is generally accompanied by depletion coefficients $A^{MAS}$ of up to 30 (in words: thirty) and more (in the case of a wash column removal, this corresponds to values of $A^{MAS}$ of at least $\geqq 100$, in favorable cases of $\geqq 1000$), while, in the converse case of a crystallizative removal of acrylic acid from liquid phase comprising methacrylic acid as the main constituent and target product, and acrylic acid as the secondary component, the acrylic acid depletion coefficients $A^{AS}$ are generally $\leqq 15$. These findings are unexpected. They are unexpected in particular because pure acrylic acid (m.p.=14° C.) and pure methacrylic acid (m.p.=15° C.) have virtually identical melting points (at pressure 1 bar) (cf., for example, Römpps Chemie-Lexikon). In contrast, their boiling behavior at standard pressure (acrylic acid b.p.=141° C., methacrylic acid b.p.=161° C.) differs substantially more markedly and suggests, for example, a rectificative removal of methacrylic acid. The aforementioned physical facts also demonstrate that, in the crystallizative purifications of acrylic acid which are generally carried out in the prior art, said acrylic acid having already been prepurified by means of other thermal separation processes (cf., for example, EP-A 616 998), acrylic acids are further purified which are entirely free of methacrylic acid. In this document, free of methacrylic acid means that methacrylic acid can no longer be detected by gas chromatography.

With the aforementioned experimental findings, the inventive procedure opens up the possibility, on the route to the preparation of glacial acrylic acid suitable for superabsorbents, of removing the methacrylic acid impurities which obstruct such a use in a single separation step, in a single crystallization stage in a satisfactory manner.

The phrase "liquid phase P (or gas mixture or product gas mixture) comprising acrylic acid as a main constituent and target product, and methacrylic acid as a secondary component" is intended in this document merely to mean that the liquid phase P (or the gas mixture or product gas mixture) comprises acrylic acid and methacrylic acid in a molar ratio V of acrylic acid to methacrylic acid of at least 3:2. V in the process according to the invention may of course also be at least 2:1, or at least 3:1, or at least 4:1, or at least 5:1, or at least 6:1, or at least 7:1, or at least 8:1, or at least 9:1, or at least 10:1. The process according to the invention is also appropriate when V is at least 15:1, or at least 20:1, or at least 25:1, or at least 30:1, or at least 35:1, or at least 40:1, or at least 45:1, or at least 50:1, or at least 60:1, or at least 70:1, or at least 80:1, or at least 90:1, or at least 100:1.

In many cases relevant to the application, V will be at least 200:1, or at least 300:1, or at least 400:1, or at least 500:1, or at least 600:1, or at least 700:1, or at least 800:1, or at least 900:1, or at least 1000:1.

However, the process according to the invention is also important when V is at least 2000:1, or at least 3000:1, or at least 4000:1, or at least 5000:1, or at least 6000:1, or at least 7000:1, or at least 8000:1, or at least 9000:1, or at least 10 000:1. V in the process according to the invention may of course also be at least 20 000:1, or at least 30 000:1, or at least 40 000:1, or at least 50 000:1, or at least 60 000:1, or at least 70 000:1, or at least 80 000:1, or at least 90 000:1, or at least 100 000:1.

In other words, the process according to the invention is still significant especially in the context of an industrial-scale preparation of acrylic acid when the liquid phase P (or the gas mixture or product gas mixture), based on its content of acrylic acid, comprises only 10 ppm by weight of methacrylic acid.

In other words, V in the process according to the invention may, for example, be from 3:2 to 100 000:1, or from 2:1 to 70 000:1, or from 3:1 to 50 000:1, or from 4:1 to 30 000:1, or from 5:1 to 10 000:1, or from 6:1 to 8000:1, or from 7:1 to 6000:1, or from 8:1 to 5000:1, or from 9:1 to 2000:1, or from 10:1 to 1000:1, or from 20:1 to 800:1, or from 30:1 to 600:1, or from 40:1 to 400:1, or from 50:1 to 300:1, or from 60:1 to 200:1, or from 70:1 to 100:1.

The above remarks are relevant especially when the liquid phase P comprises at least 10% by weight of acrylic acid, or at least 20% by weight of acrylic acid, or at least 30% by weight of acrylic acid, or at least 40% by weight of acrylic acid, or at least 50% by weight of acrylic acid, or at least 60% (or at least 65%) by weight of acrylic acid, or at least 70% by weight of acrylic acid, or at least 80% by weight of acrylic acid, or at least 90% by weight of acrylic acid, or at least 93% by weight of acrylic acid, or at least 94% by weight of acrylic acid, or at least 95% by weight of acrylic acid, or at least 96% by weight of acrylic acid, or at least 97% by weight of acrylic acid, or at least 98% by weight of acrylic acid, or at least 99% by weight of acrylic acid, or at least 99.5% by weight of acrylic acid, or at least 99.7% by weight of acrylic acid, or at least 99.9% by weight of acrylic acid, or at least 99.95% by weight of acrylic acid, or even more acrylic acid.

Based on the amounts of acrylic acid comprised in the aforementioned liquid phases P, their methacrylic acid content may, in a manner typical of the process according to the invention, be from 0.001 to 15% by weight, or from 0.01 to 15% by weight, or from 0.02% by weight to 10% by weight, or from 0.03% by weight to 7% by weight, or from 0.04% by weight to 5% by weight, or from 0.05% by weight to 3% by weight, or from 0.07% by weight to 2% by weight, or from 0.09% by weight to 1.5% by weight, or from 0.1 or 0.15 to 1 or to 0.5% by weight.

Whether acrylic acid crystals separate out or not in the course of cooling of liquid phases P having such a composition depends in the individual case upon the overall composition of the liquid phase P. According to the teaching of WO 03/078378, this may be the case even for liquid phases P which comprise from 0.5 to 90% by weight, or from 7 to 50% by weight, or from 10 to 25% by weight, or else from 10 to 85% by weight, or from 15 to 80% by weight, or from 25 to 75% by weight, of water.

EP-A 002 612 discloses that the eutectic of water-acrylic acid is eliminated, for example, by addition of salts to give aqueous acrylic acid solutions and thus that a crystallization of acrylic acid can be brought about even at relatively low acrylic acid contents (this auxiliary measure may also be employed in the process according to the invention).

In a similar manner, WO 99/06348 recommends the addition of polar organic substances before a crystallizative acrylic acid removal from aqueous phases P (this auxiliary measure may also be employed in the process according to the invention).

DE-A 198 38 845 teaches that acrylic acid is generally separated in the course of cooling from liquid phases P which comprise acrylic acid and an organic solvent having a higher boiling point than acrylic acid under standard conditions when the liquid phase P comprises from >60 to <99.9% by weight of acrylic acid, from 0.1 to 40% by weight of high-boiling organic solvent and from >0 to 35% by weight of secondary components obtained in the catalytic acrylic acid preparation in the gas phase. The liquid phases P of DE-A 198 38 845, which forms an integral part of this document, are also useful for the process according to the invention provided that they have the methacrylic acid impurity required in accordance with the invention.

According to the above, it can be assumed that acrylic acid regularly crystallizes out at least in the course of cooling of liquid phases P which comprise ≧65% by weight of acrylic acid and are to be treated in accordance with the invention.

The process according to the invention can therefore be applied advantageously in particular to liquid phases P contaminated with methacrylic acid when they comprise from 65 to 99.5% by weight, or from 70 to 99.5% by weight, or from 80 to 99.5% by weight, or from 85 to 99% by weight, or from 90 to 98% by weight, or from 93 to 97% by weight, of acrylic acid. This is the case in particular when the methacrylic acid contents, based on acrylic acid comprised, are simultaneously from 0.01 to 15% by weight, or from 0.02 to 10% by weight, or from 0.03 to 7% by weight, or from 0.04 to 5% by weight, or from 0.05 to 3% by weight, or from 0.07 to 2% by weight, or from 0.09 to 1.5% by weight, or from 0.1 or 0.15 to 1 or to 0.5% by weight.

Otherwise, liquid phases P to be treated in accordance with the invention may, in a manner known per se, be obtained from (stem from) product gas mixtures, comprising acrylic acid as a main constituent and methacrylic acid as a secondary component, of heterogeneously catalyzed partial oxidations of $C_3$ precursors of acrylic acid contaminated, for example, in the manner described (propane, propylene and/or acrolein; possible $C_3$ precursors also include propionic acid, propanol and/or propionaldehyde; in this case, the partial oxidation is a heterogeneously catalyzed oxydehydrogenation) as already described in the prior art. The remaining composition of these product gas mixtures will substantially be that as known from the known oxidative acrylic acid preparations in the gas phase. In addition, the inventive crystallization process may be practiced in the same way and be integrated in the same way into the overall process for removing (glacial) acrylic acid from the product mixture, as taught in particular by the following prior art documents, all of which are an integral part of this document (typical methacrylic acid contents of such product gas mixtures are, based on the amount of acrylic acid comprised therein, for example from 0.01 to 15% by weight, or to 10% by weight, or to 5% by weight, frequently from 0.02 to 4% by weight, in many cases from 0.03 to 3% by weight, often from 0.04 to 2% by weight, but also from 0.05 to 1% by weight, or from 0.07 to 0.75% by weight, or from 0.1 to 0.5% by weight, or from 0.2 to 0.4% by weight): WO 02/055469, WO 03/078378, WO 01/77056, WO 03/041833, DE-A 196 06 877, DE-A 103 36 386, WO 98/01414, WO 01/77056, EP-A 14 84 308, EP-A 14 84 309, US-A 2004/0242826, DE-A 102 43 625, DE-A 196 06 877, EP-A 792 867, EP-A 10 15 410, EP-A 920 408, EP-A 11 89 861, EP-A 10 15 411, EP-A 10 68 174, WO 2004/035514, EP-A 10 66 293, EP-A 11 163 201, EP-A 1159 249; WO 02/090310, DE-A 101 22 787, WO 03/041832, DE-A 102 35 847, EP-A 12 52 129, EP-A 616 998, EP-A 13 88 533, EP-A 11 25 912 and EP-A 11 16 709.

The process according to the invention is of very particular significance when the liquid phase P which comprises acrylic acid as a main constituent and target product, and methacrylic acid as a secondary component, and is to be treated in accordance with the invention is obtained from the product gas mixture of a heterogeneously catalyzed partial gas phase oxidation of at least one $C_3$ precursor of acrylic acid using at least one indistinct separation process. This is the case especially when the mother liquor remaining in the subsequent crystallizative removal of the remaining methacrylic acid is recycled at least partly into at least one of the indistinct separation processes.

The basic structure of such a combined use of indistinct separation processes and the distinct separation process of crystallization is taught, for example, by DE-A 196 06 877, EP-A 792 867, and also EP-A 14 84 308, EP-A 14 84 309, EP-A 11 16 709 and in particular EP-A 10 15 410.

An indistinct separation process is defined as a separation process in which the composition of the phase which is formed when the separation process is employed and comprises accumulated target product is dependent markedly upon the composition of the mixture to be separated, while the inventive crystallizative treatment is a distinct separation process to the extent that the composition of the acrylic acid crystals which form is substantially independent (ideally there is complete independence) of the composition of the liquid phase P.

In the case of such a combination of a distinct and an indistinct separation process, the process according to the invention is of increased significance in as far as, in the continuous operation of such a procedure, the methacrylic acid accumulates in the liquid phase P to be treated in accordance with the invention as a result of the mother liquor recycling, since the mother liquor comprises the methacrylic acid in accumulated form. In other words, even comparatively small methacrylic acid contents in the product gas mixture of the gas phase oxidation can thus grow to become a serious problem. Increased methacrylic acid contents may also be comprised in liquid phases P, for example, when mother liquors obtained in the process according to the invention are crystallized further for the purpose of increasing the yield, or when methacrylic acid-comprising secondary streams obtained in the indistinct separation process are treated in accordance with the invention to increase the yield.

This means that, in the case of depletion coefficients $A^{MAS}<15$, such a procedure would be extremely inefficient. The efficiency required on the industrial scale is gained only by, surprisingly in accordance with the invention, an $A^{MAS}$ of >15 having been found.

In general, the at least one indistinct separation process employed to obtain the liquid phase P to be treated in accordance with the invention from the product gas mixture of a heterogeneously catalyzed partial gas phase oxidation of at least one $C_3$ precursor of acrylic acid will be a distillation, rectification, absorption, adsorption, extraction, desorption, stripping, distraction, (partial) condensation, fractional condensation, a membrane separation process such as a pervaporation/vapor permeation or a combination of such processes.

Particularly frequently, a distillation, rectification, absorption, extraction, partial condensation, fractional condensation, desorption, stripping and/or distraction will be employed. Frequently, the liquid phase P to be treated in accordance with the invention will be obtained by employing the aforementioned processes repeatedly.

In the simplest case, the liquid phase P to be treated in accordance with the invention may be the absorbent and/or partial condensate and/or condensate obtained by fractionation, of an absorptive and/or condensative removal of acrylic acid from the product gas mixture of a heterogeneously catalyzed partial gas phase oxidation of at least one of the $C_3$ precursors listed in this document. In that case, preference is given in accordance with the invention to mother liquor being recycled into the absorption and/or condensation.

In an appropriate manner, a combination of indistinct and distinct separation to be employed as described has an outlet for at least one stream comprising accumulated methacrylic acid. Advantageously in accordance with the invention, this is on the side of the indistinct separation process. In general, the bottoms liquid of a separation column will be used as such an outlet, from which column the liquid phase P itself or the stream to be converted later to the liquid phase P is withdrawn, for example, via side withdrawal and/or via top withdrawal.

However, a methacrylic acid outlet may be disposed also or only on the side of the inventive removal, i.e. on the crystallizative side. In this case, the outlet will consist of mother liquor comprising accumulated methacrylic acid.

When the inventive removal is performed, for example, by means of a combination of dynamic and static crystallization according to EP-A 616998, the mother liquor outlet comprising accumulated methacrylic acid will be disposed in the region of the static crystallization. The latter is the case in particular when no mother liquor recycling into an indistinct separation is carried out when the process according to the invention is employed.

The process according to the invention is favorable not least when the liquid phase P to be treated in accordance with the invention (for example by means of one of the above-described procedures) stems from a product gas mixture of a partial oxidation of at least one $C_3$ precursor of acrylic acid, comprises the methacrylic acid in the already stated contents based on the acrylic acid content of the product gas mixture, and otherwise comprises:

from 1 to 30% by volume of acrylic acid, from $\geq 0$ or 0.005 to 10% by volume of propylene, from $\geq 0$ or 0.001 to 2% by volume of acrolein, from $\geq 0$ or 0.001 to 2% by volume of methacrolein, from $\geq 0$ or 0.005 to 10% by volume of molecular oxygen, from $\geq 0$ or 0.005 to 3% by volume of acetic acid, from $\geq 0$ or 0.001 to 2% by volume of propionic acid, from $\geq 0$ or 0.001 to 2% by volume of formaldehyde, from $\geq 0$ or 0.0001 to 2% by volume of other aldehydes, and from 10 to 98% by volume or from 50 to 98% by volume of (inert) diluent gases.

The diluent gases may comprise:

from $\geq 0$ or 0.005 to 90% by volume of saturated $C_1$- to $C_6$-hydrocarbons (especially propane, methane and/or ethane), from $\geq 0$ or 0.05 to 30% by volume of steam, from $\geq 0$ or 0.05 to 15% by volume of carbon oxides (CO and/or $CO_2$), and from $\geq 0$ or 1 to 90% by volume of molecular nitrogen.

The partial oxidation product gas mixture may in particular stem from a partial oxidation as described in the documents DE-A 10 2004 032 129 and their equivalent foreign patents, DE-A 10245585, WO 03/076370, WO 01/96271, EP-A 117146, WO 03/011804, U.S. Pat. No. 3,161,670, DE-A 3313573, DE-A 10316039 and WO 01/96270, starting from propylene and/or propane, and has as the propylene source, if appropriate, a propane dehydrogenation and/or oxydehydrogenation (heterogeneously catalyzed if appropriate) as a preceding reaction stage.

A representative example (i.e. just one possible example) of such a product gas mixture composition is a product gas mixture which comprises (all secondary components listed would be removed satisfactorily when the process according to the invention is employed if they had been a constituent of the liquid phase P):

|  | % by vol. |
|---|---|
| nitrogen | 51.54 |
| oxygen | 2.3 |
| propane | 29.20 |
| propene | 0.110 |
| methane | 0 |
| ethane | 0.077 |
| n-butane | 0.101 |
| isobutane | 0.236 |
| n-butenes | 0 |
| isobutene | 0.001 |
| 1,3-butadiene | 0.009 |
| hydrogen | 0.05 |
| carbon monoxide | 0.596 |
| carbon dioxide | 1.72 |
| water | 8.21 |
| acrolein | 0.09 |
| acrylic acid | 5.28 |
| acetic acid | 0.240 |
| propionic acid | 0.002 |
| formic acid | 0.019 |
| formaldehyde | 0.198 |
| benzaldehyde | 0.005 |
| maleic anhydride | 0.047 |
| methacrolein | 0.020 |
| methacrylic acid | 0.011 and |
| ethene | 0.032. |

Advantageously in accordance with the invention, the liquid phase P to be treated in accordance with the invention will be obtained from the aforementioned product gas mixtures of the $C_3$ acrylic acid precursor partial oxidation by condensing acrylic acid out of the product gas mixture. Advantageously in accordance with the invention, the condensate obtained directly forms the liquid phase P. Advantageously, the condensation of acrylic acid out of the product gas mixture (which has been cooled beforehand if appropriate) is effected as a fractional condensation (on which is, if appropriate, additionally superimposed an absorption with water and/or aqueous solution in order to reduce acrylic acid losses) as described in detail, for example, in the documents EP-A 1015410, WO 2004/035514, DE-A 10243625, EP-A 1015411, DE-A 10235847, EP-A 1159249, EP-A 1163201, EP-A 1066239 and EP-A 920408.

In this condensation, the product gas mixture is appropriately, if appropriate after preceding direct and/or indirect cooling (for example with a quenched liquid according to EP-A 1066239, or according to EP-A 1163201), fractionally condensed in a separating column having separating internals, ascending into itself with side draw removal of crude acrylic acid (which preferably forms the liquid phase P to be treated in accordance with the invention; if appropriate the crude acrylic acid is also treated rectificatively and/or distillatively to obtain the liquid phase P).

Liquid phase P obtained condensatively (and if appropriate additionally rectificatively) in this way can then be treated crystallizatively in accordance with the invention. Mother liquor comprising accumulated methacrylic acid which is formed will, according to the model, for example, of EP-A 920408 or WO 2004/035514, be recycled at least partly, preferably fully, into the condensation of acrylic acid out of the product gas mixture. The methacrylic acid outlet will be located below the side draw of the crude acrylic acid.

Liquid phase P which has been obtained in this way by partial or total condensation and/or superimposed absorption with water or aqueous solution and also, if appropriate, rectificative aftertreatment, and is to be treated in accordance with the invention, may, in addition to the contents of methacrylic acid based on acrylic acid comprised which have already been indicated (and are essential to the invention), comprise:

from 65, or 75, or 85 to 99.5% by weight of acrylic acid, from $\geq 0$, generally from 0.1 to 40% by weight of water, from $\geq 0$, in general from 0.001 to 5% by weight of acrolein, from $\geq 0$, in general from 0.001 to 10% by weight of methacrolein, from $\geq 0$, in general from 0.01 to 5% by weight of acetic acid, from $\geq 0$, in general from 0.01 to 5% by weight of propionic acid, from $\geq 0$, in general from 0.001 to 5% by weight of formaldehyde, from $\geq 0$, in general from 0.001 to 5% by weight of further aldehydes (per aldehyde), and from $\geq 0$, in general from 0.01 to 5% by weight of maleic acid.

Advantageously, the aforementioned contents of the liquid phase P will be:

from 93 to 98% by weight of acrylic acid, from 1 to 5% by weight of water, from 0.001 to 3% by weight of acrolein, from 0.001 to 3% by weight of methacrolein, from 0.1 to 3% by weight of acetic acid, from 0.01 to 3% by weight of propionic acid, from 0.001 to 3% by weight of formaldehyde, from 0.001 to 3% by weight of further aldehydes (per aldehyde) and from 0.01 to 3% by weight of maleic acid.

Following the specifications of WO 02/055469 and WO 03/078378, it may also comprise up to 3% by weight of protoanemonin.

The inventive crystallizative treatment of the liquid phase P, especially of a liquid phase P obtained condensatively and/or absorptively and/or rectificatively in the aforementioned manner, is in principle subject to no restriction, including the process for removing the mother liquor from the crystals (all processes detailed in the prior art mentioned can be employed).

In other words, it may be carried out in one or more stages, continuously or batchwise. In particular, it may also be carried out as a fractional crystallization. Typically, in a fractional crystallization, all stages which generate acrylic acid crystals which are purer (especially freer from methacrylic acid) than the liquid phase P supplied are known as purification stages and all other stages stripping stages. Appropriately, multistage processes are operated by the countercurrent principle, in which, after the crystallization in each stage, the crystals are removed from the mother liquor and these crystals of the particular stage are fed with the next highest degree of purity, while the crystallization residue of the particular stage is fed with the next lowest degree of purity.

In general, the temperature of the liquid phase P during the process according to the invention is between −25° C. and +14° C., in particular between 12° C. and −5° C.

For example, the process according to the invention may be performed as a layer crystallization (cf. DE-A 2606364, EP-A 616998, EP-A 648520 and EP-A 776875). In this crystallization, the crystals are frozen out in the form of continuous, firmly adhering layers. The deposited crystals are separated from the remaining residual melt (the mother liquor) by virtue of the residual melt simply flowing off. In principle, a distinction is drawn between "static" and "dynamic" layer crystallization processes. A characteristic feature of dynamic layer crystallization of liquid phases P is forced convection of the liquid phase P. This can be effected by pumped circulation of the liquid phase through tubes with full flow-through, by introduction of the liquid phase P as a trickle film (for example according to EP-A 616998) or by introduction of inert gas into a liquid phase P or by pulsation.

In the static processes, the liquid phase P is at rest (for example in tube bundle or plate heat exchangers) and deposits in layers as result of slow temperature reduction on the secondary side. Afterward, the residual melt (mother liquor) is discharged, more highly contaminated fractions are sweated off from the crystal layer by slow temperature increase and the pure product is subsequently melted off (cf. WO 01/77056).

According to the invention, the process according to the invention, in the case of all liquid phases P described in this document, will, however, preferably be performed according to the teaching of WO 01/77056, WO 02/055469 and WO 03/078378 as a suspension crystallization.

In general, a crystal suspension comprising suspended acrylic acid crystals is obtained by cooling the liquid phase P, the acrylic acid crystals having a lower methacrylic acid content and the remaining residual melt (mother liquor) a higher methacrylic acid content (relatively, based on the particular total amount) than the liquid phase P to be purified. The acrylic acid crystals may grow directly in suspension and/or be deposited as a layer on a cooled wall from which they are subsequently scratched off and resuspended in the residual melt (mother liquor).

All suspension crystallizers and suspension crystallization processes detailed in WO 01/77056, WO 02/055469, and WO 03/078378 are useful in accordance with the invention. In general, the acrylic acid crystal suspension generated has a solids content of from 20 to 40% by weight.

In addition, all processes specified in the aforementioned WO publications are suitable for the separation of suspension crystals which have formed and mother liquor which remains (for example mechanical separation processes such as centrifugation). Preference is given in accordance with the invention to separating in a wash column. This is preferably a wash column with forced transport of the deposited acrylic acid crystals. The crystal volume fraction in the crystal bed generally attains values of >0.5. In general, the wash column is operated at values of from 0.6 to 0.75. The wash liquid used is advantageously the melt of acrylic acid crystals purified (removed) beforehand in the wash column. The washing is normally effected in countercurrent. The process according to the invention thus in particular comprises processes which comprise the following process steps:

a) crystallization of acrylic acid out of a liquid phase P;

b) separation of the acrylic acid crystals from the remaining mother liquor (residual melt, liquid residual phase);

c) at least partial melting of the removed acrylic acid crystals and d) at least partial recycling of the molten acrylic acid crystals to step b) and/or to step a).

Preference is given to effecting step b) by countercurrent washing with acrylic acid crystals which have been removed beforehand, melted and recycled into step b).

Advantageously in accordance with the invention, the liquid phase P comprises water when the process according to the invention is employed, since formation of acrylic acid crystals in the presence of water, according to the teaching of WO 01/77056 and WO 03/078378, causes a particularly favorable crystal form for the subsequent separation of the crystals from the remaining mother liquor. This is especially true when the crystallization is performed as a suspension crystallization, and even more true when the subsequent mother liquor removal is performed in a wash column, and even more true when the wash liquid used is the melt of acrylic acid crystals which have already been purified in the wash column.

In other words, the process according to the invention comprises in particular processes in which the liquid phase P to be purified is converted under the action of cold conditions to a crystal suspension consisting of acrylic acid crystals and liquid residual phase (residual melt), the proportion by weight of methacrylic acid in the acrylic acid crystals being smaller and the proportion by weight of the liquid residual phase (the mother liquor) of methacrylic acid being greater than the proportion by weight of methacrylic acid in the liquid phase P, a portion of the remaining mother liquor is removed mechanically if appropriate from the crystal suspension, and the acrylic acid crystals are freed in a wash column of remaining mother liquor, with the proviso that a) the liquid phase P, based on the acrylic acid comprised therein, comprises from 0.20 to 30% by weight, frequently up to 20% by weight, often up to 10% by weight, of water, and b) the wash liquid used is the melt of acrylic acid crystals purified in the wash column.

In particular, the process according to the invention comprises the aforementioned processes, the liquid phase P comprising $\geq 80\%$ by weight of acrylic acid, or $\geq 90\%$ by weight of acrylic acid or $\geq 95\%$ by weight of acrylic acid. The molar ratio V in the liquid phase P to be purified may in each case have all of the values specified in this document.

Moreover, it is advantageous in accordance with the invention when the water content of the liquid phase P in the above-described procedures (or quite generally when the process according to the invention is employed), based on acrylic acid comprised in the liquid phase P, is from 0.2 or 0.4 to 8, or to 10, or to 20, or to 30% by weight, or from 0.6 to 5% by weight, or from 0.60 to 3% by weight.

The process according to the invention can of course also be applied to all crude acrylic acids of WO 98/01414, provided that they additionally comprise methacrylic acid as a secondary component.

All of the aforementioned applies in particular when the wash column is a wash column having forced transport of the acrylic acid crystals, in particular when it is a hydraulic or a mechanical wash column according to WO 01/77056 and is operated as detailed therein.

All of the aforementioned is true in particular when the wash column is designed and operated according to the teachings of WO 03/041832 and of WO 03/041833.

The process according to the invention thus permits, with the sequence of partial oxidation of at least one $C_3$ precursor, fractional acrylic acid condensation from the product gas mixture of the partial oxidation, suspension crystallization of the acrylic acid condensate withdrawn and removal of the suspension crystals from remaining mother liquor in a wash column using a pure crystal melt as the wash liquid, the preparation of acrylic acid suitable for superabsorbents in a highly efficient manner and using only one crystallization stage (such acrylic acid can of course also be used for all other uses addressed in WO 02/055469 and WO 03/078378, even when the starting material for the partial oxidation is a cheap $C_3$ precursor raw material source which causes the by-product formation of methacrylic acid).

Of course, all process steps detailed in this document are carried out with polymerization inhibition. The procedure may be as described in the prior art listed. An excellent position among the entirety of the available acrylic acid process stabilizers is assumed by dibenzo-1,4-thiazine (PTZ), 4-hydroxy-2,2,6,6-tetramethylpiperidine 1-oxyl (4-OH-TEMPO) and p-methoxyphenol (MEHQ), which either alone, or in pairs or as a three-substance mixture may be part of the liquid phase P to be treated in accordance with the invention. Typically, the total amount of polymerization inhibitors comprised in the liquid phase P, based on the total amount of acrylic acid and methacrylic acid comprised therein, is from 0.001 to 2% by weight.

Owing to undesired formation of acrylic acid oligomers (Michael adducts) in the liquid phase P when it is left alone, the process according to the invention is employed as promptly as possible after generation of the liquid phase P.

In an advantageous manner in accordance with the invention, when the process according to the invention is employed, other $C_4$ (e.g. butene-1, butadiene, n-butane, etc.) subsequent partial oxidation products comprised in the liquid phase P, for example methacrolein, butyric acids, butyraldehydes, etc. are also removed. Based on acrylic acid, they may be present in the same amounts as methacrylic acid in the liquid phase P (in particular in all liquid phases P detailed explicitly in this document). The same applies to propionaldehyde and all $C_5$ and $C_6$ subsequent partial oxidation products.

EXAMPLES AND COMPARATIVE EXAMPLE

Comparative Example 430 g of a methacrylic acid were charged with a temperature of 25° C. into a stirred glass vessel (internal volume 1 l) with jacket cooling. The stirring was effected by means of a close-clearance helical stirrer.

The methacrylic acid comprised:

69.1% by weight of methacrylic acid, 18.2% by weight of water, 3.6% by weight of acetic acid and 0.5% by weight of acrylic acid.

It was obtained by heterogeneously catalyzed gas phase partial oxidation of methacrolein and subsequent fractional condensation of the product gas mixture. Addition of less than 200 ppm by weight of hydroquinone (based on the sum of acrylic acid and methacrylic acid) inhibited the methacrylic acid to polymerization.

At a cooling rate of 0.5 K/h, the temperature of the cooling liquid conducted within the jacket (water/glycol or water/ethanol mixture) was reduced until the resulting crystal suspension (methacrylic acid crystals suspended in residual melt) had a solids content of 16% by weight. A portion of the crystal suspension was then withdrawn and centrifuged at 2000 rpm on a laboratory centrifuge in a sieve cup equipped with a polypropylene filter fabric for 30 seconds. This centrifuged off the majority of mother liquor remaining. Subsequently, the mother liquor removal was completed by once again centrifuging as described for 30 seconds and washing the crystals simultaneously with a methacrylic acid (methacrylic acid content >98% by weight, acrylic acid content <0.1% by weight, temperature of this wash methacrylic acid=25° C.) in a weight ratio of 1:1. Analysis of the remaining crystals and of the mother liquor centrifuged off beforehand gave the following depletion coefficients A for the different secondary components comprised in the methacrylic acid:

| Secondary component | A |
|---|---|
| Water | 41.7 |
| Acetic acid | 33.3 |
| Acrylic acid | 9.09 |

In contrast to water and acetic acid, acrylic acid is incorporated into the deposited methacrylic acid crystals.

Examples

In each case approx. 1800 g of various acrylic acids were charged into a stirred metal tank (internal volume 2 l, close-clearance helical stirrer). They were polymerization-inhibited by addition of from 100 to 200 ppm by weight of monomethyl ether of hydroquinone (MEHQ) and <100 ppm by weight of phenothiazine (based on acrylic acid comprised).

At a cooling rate of 1 K/h, the temperature of the cooling liquid within the jacket was lowered until the resulting crystal suspension (acrylic acid crystals suspended in residual melt) had a solids content of in each case approx. 18% by weight. A portion of the crystal suspension was then withdrawn and centrifuged at 2000 rpm on a laboratory centrifuge as in the comparative example for 180 seconds, and the remaining mother liquor was thus virtually fully centrifuged off. Analysis of the remaining crystals and of the mother liquor which had been centrifuged off gave the depletion coefficients listed below for the different contaminated acrylic acids (liquid phases P to be treated in accordance with the invention) for the secondary components comprised therein. The acrylic acids were obtained starting from acrylic acid stemming from a heterogeneously catalyzed gas phase partial oxidation of propylene having a small $C_4$ fraction by addition of glacial methacrylic acid thereto. The starting acrylic acid comprised the following contents:

95.201% by weight of acrylic acid, 0.042% by weight of methacrylic acid, 0.604% by weight of benzaldehyde, 0.062% by weight of propionic acid, 0.687% by weight of furan-2-aldehyde, 0.663% by weight of acetic acid, 0.004% by weight of furan-3-aldehyde, 0.002% by weight of allyl acrylate, 0.009% by weight of acrolein and 2.20% by weight of water.

This acrylic acid was admixed once with 0.2% by weight of methacrylic acid (sample 1), once with 1% by weight of methacrylic acid (sample 2) and once with 5% by weight of methacrylic acid (sample 3) (based in each case on the weight of the starting acrylic acid) and the different samples were treated as described. In the same manner, the starting acid itself was treated. The depletion coefficients determined for the secondary components comprised in the different samples and in the starting acid were as follows:

| secondary component | A (sample 1) | A (sample 2) | A (sample 3) | A (starting acid) |
|---|---|---|---|---|
| methacrylic acid | 31.3 | 45.5 | 30.3 | no longer detectable in the crystals |
| benzaldehyde | 31.3 | 45.4 | 31.2 | 31.2 |
| propionic acid | 3.9 | 4.1 | 3.85 | 3.86 |
| furan-2-aldehyde | 31.3 | 47.6 | 30.3 | 31.25 |
| acetic acid | 5.8 | 6.4 | 5.59 | 5.85 |

Remarkably, the ratios are reversed from the case of the comparative example. While acetic acid and propionic acid are incorporated here, this is the case neither for methacrylic acid nor the two aldehydes.

U.S. Provisional Patent Application Nos. 60/668,089, filed on Apr. 5, 2005, and 60/656,877, filed on Mar. 1, 2005, are incorporated into the present application by literature reference. With regard to the abovementioned teachings, numerous alterations and deviations from the present invention are possible. It can therefore be assumed that the invention, within the scope of the appended claims, can be performed in a different way from that specifically described herein.

What is claimed is:

1. A process for removing methacrylic acid from acrylic acid in a liquid phase P comprising acrylic acid and methacrylic acid with an acrylic acid content of at least 50% by weight and a molar ratio V of acrylic acid to methacrylic acid ranging from 3:2 to 100 000:1, which comprises:
    subjecting liquid phase P to crystallization thereby forming acrylic acid crystals and a mother liquor that contains methacrylic acid.

2. The process according to claim 1, wherein the liquid phase P comprises at least 65% by weight of acrylic acid.

3. The process according to claim 1, wherein the liquid phase P, based on the amount of acrylic acid comprised therein, comprises from 0.01 to 15% by weight of methacrylic acid.

4. The process according to claim 1, wherein the liquid phase P comprises from 65 to 99.5% by weight of acrylic acid.

5. The process according to claim 1, wherein the liquid phase P, based on the acrylic acid therein, comprises from 0.2 to 30% by weight of water.

6. The process according to claim 1, wherein the liquid phase P stems from the product gas mixture of a heterogeneously catalyzed gas phase partial oxidation of at least one $C_3$ precursor compound of acrylic acid.

7. The process according to claim 6, wherein the at least one $C_3$ precursor compound is propane.

8. The process according to claim 6, wherein the at least one $C_3$ precursor compound is propylene.

9. The process according to claim 6, wherein the at least one $C_3$ precursor compound is propylene accompanied by propane as an inert gas constituent.

10. The process according to claim 9, wherein the propylene and the accompanying propane are constituents of the product gas mixture obtained from the partial dehydrogenation and/or oxydehydrogenation of propane which precedes the gas phase partial oxidation.

11. The process according to claim 1, wherein the liquid phase P stems from the product gas mixture of a heterogeneously catalyzed gas phase partial oxidation of at least one $C_3$ precursor compound of acrylic acid and is obtained therefrom by at least one indistinct separation process.

12. The process according to claim 11, wherein the at least one indistinct separation process comprises at least one separation process which is an absorption process, a partial condensation process, a fractional condensation process, a rectification process, a stripping process, or a desorption process.

13. The process according to claim 11, wherein said mother liquor comprising accumulated methacrylic acid is recycled into at least one of the at least one indistinct separation process.

14. The process according to claim 13, wherein said mother liquor comprising accumulated methacrylic acid is recycled into a fractional condensation of the product gas mixture of the heterogeneously catalyzed gas phase partial oxidation of the at least one $C_3$ precursor compound of acrylic acid.

15. The process according to claim 1, wherein the crystallization of acrylic acid which accomplishes the removal of acrylic acid is done by suspension crystallization.

16. The process according to claim 15, wherein the separation of suspended crystals from mother liquor which forms is accomplished by means of a wash column.

17. The process according to claim 16, wherein the wash liquid used is the melt of acrylic acid crystals removed beforehand in the wash column.

18. The process according to claim 1, which comprises the following process steps:
   a) crystallizing acrylic acid from liquid phase P, thereby forming crystals of acrylic acid and a mother liquor;
   b) separating the acrylic acid crystals from the mother liquor;
   c) at least partially melting the removed acrylic acid crystals and
   d) at least partially recycling the molten acrylic acid crystals to step b) and/or to step a).

19. The process according to claim 1, which is followed by a process in which acrylic acid crystals are melted and free-radically polymerized to polymers.

20. The process according to claim 1, wherein liquid phase P is comprised of:
   from 65 to 99.5% by weight of acrylic acid,
   from $\geq 0$ to 40% by weight of water,
   from $\geq 0$ to 5% by weight of acrolein,
   from $\geq 0$ to 10% by weight of methacrolein,
   from $\geq 0$ to 5% by weight of acetic acid,
   from $\geq 0$ to 5% by weight of propionic acid,
   from $\geq 0$ to 5% by weight of formaldehyde,
   from $\geq 0$ to 5% by weight of other aldehydes (per aldehyde), and
   from $\geq 0$ to 5% by weight of maleic acid.

21. The process according to claim 20, wherein liquid phase P is comprised of:
   from 93 to 98% by weight of acrylic acid,
   from 1 to 5% by weight of water,
   from 0.001 to 3% by weight of acrolein,
   from 0.001 to 3% by weight of methacrolein,
   from 0.1 to 3% by weight of acetic acid,
   from 0.01 to 3% by weight of propionic acid,
   from 0.001 to 3% by weight of formaldehyde,
   from 0.001 to 3% by weight of further aldehydes (per aldehyde) and
   from 0.01 to 3% by weight of maleic acid.

22. The process according to claim 1, wherein molar ratio V ranges from 2:1 to 70,000:1.

23. The process according to claim 1, wherein molar ratio V ranges from 3:1 to 50,000:1.

24. The process according to claim 1, wherein molar ratio V ranges from 4:1 to 30,000:1.

* * * * *